United States Patent [19]

Nishida et al.

[11] 4,026,960

[45] May 31, 1977

[54] 2,7,10,15,18,23-HEXAMETHYLTETRACOSANE

[75] Inventors: Takashi Nishida; Yoichi Ninagawa; Kazuo Itoi, all of Kurashiki; Yoshiaki Omura, Okayama; Yoshin Tamai, Kurashiki; Takeo Hosogai, Kiyone; Yoshiji Fujita, Kurashiki, all of Japan

[73] Assignee: Kuraray Co., Ltd., Kurashiki, Japan

[22] Filed: July 9, 1974

[21] Appl. No.: 486,782

[30] Foreign Application Priority Data

July 6, 1973  Japan ............... 48-76875

[52] U.S. Cl. ............... 260/676 R; 260/632 Y; 260/632 R; 260/635 M; 260/635 Y; 260/683.9

[51] Int. Cl.² ............... C07C 9/16

[58] Field of Search ............... 260/676 R

[56] References Cited

UNITED STATES PATENTS

| | | | |
|---|---|---|---|
| 3,203,998 | 8/1965 | House et al. ............... | 260/617 |
| 3,379,766 | 4/1968 | Hwang et al. ............... | 260/676 R |
| 3,501,546 | 3/1970 | Dubeck et al. ............... | 260/676 R |
| 3,542,677 | 11/1970 | Theimer ............... | 260/677 R |
| 3,576,898 | 4/1971 | Blake et al. ............... | 260/676 R |
| 3,666,827 | 5/1972 | Carlson ............... | 260/676 R |
| 3,775,503 | 11/1973 | Driscoll et al. ............... | 260/676 R |
| 3,778,487 | 12/1973 | Driscoll et al. ............... | 260/676 R |
| 3,794,692 | 2/1974 | Komatsu et al. ............... | 260/677 |
| 3,801,668 | 4/1974 | Komatsu et al. ............... | 260/677 |
| 3,923,918 | 12/1975 | Nishida et al. ............... | 260/682 |

Primary Examiner—Herbert Levine
Attorney, Agent, or Firm—Bacon & Thomas

[57] ABSTRACT 2,7,10,15,18,23-Hexamethyltetracosane is a novel compound. This compound is prepared [1] by hydrogenating 2,7,10,15,18,23-hexamethyltetracosa-1,6,18,23-tetraene-11,13-diyne-10,15-diol [itself a novel compound] or 2,7,10,15,18,23-hexamethyltetracosa-11,13-diyne-10,15-diol, dehydrating the hydrogenated intermediates, and thence hydrogenating the dehydrated precursors, or [2] by selectively, partially hydrogenating the said 10,15-diol compounds and thence hydrogenolyzing the precursor diols, or [3] by hydrogenolyzing the said 10,15-diol compounds, or [4] by hydrogenolyzing the hydrogenated intermediates of the reaction [1]. The compound, 3,6,11-trimethyl-undeca-6,11-dien-1-yl-3-ol, a starting material intermediate, is also a novel compound.

1 Claim, 1 Drawing Figure

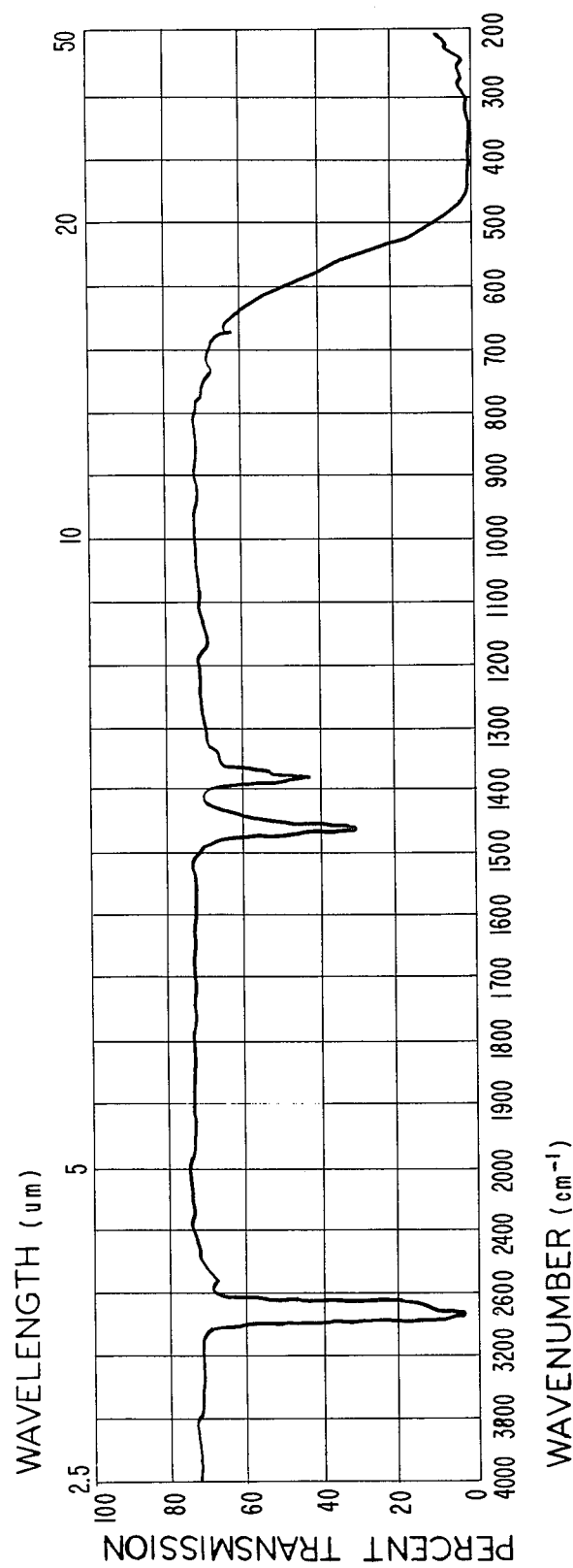

2,7,10,15,18,23-HEXAMETHYLTETRA-COSANE

BACKGROUND OF THE INVENTION

1. Field of the Invention

The present invention relates to the novel compound, 2,7,10,15,18,23-hexamethyltetracosane and to various processes for the preparation of same; additionally, the present invention relates to the fact that said 2,7,10,15,18,23-hexamethyltetracosane, akin in chemical structure to squalane [2,6,10,15,19,23-hexamethyltetracosane], has properties similar to those of squalane and is, therefore, a useful compound as an additive base or carrier material to or for various cosmetics, is a valuable substitute for squalane and also is a lubricant of note for precision machines, such as chronometers.

2. Description of the Prior Art

Heretofore, a process has been described for preparing squalane comprising reacting ketones having 13 carbon atoms, such as geranyl acetone, hexahydropseudoionone and 6,11-dimethylundeca-5,10-dien-2-one, with acetylene, to yield acetylene monoalcohols, subjecting the said monoalcohols to a coupling reaction to provide diacetylene dialcohols and thence subjecting the said dialcohols to dehydration and hydrogenation [compare Japanese patent application No. Sho 48-32274/1973], which corresponds to U.S. Pat. No. 3,923,918.

Another process for preparing squalane comprises reacting the aforesaid ketones having 13 carbon atoms with diacetylene, to obtain diacetylene dialcohols and ultimately subjecting said dialcohols to hydrogenation, dehydration and hydrogenation, or hydrogenolysis [Japanese patent applications Nos Sho 48-39667/1973 and Sho 48-48193/1973], which corresponds to U.S. patent application Ser. No. 454,694, filed Mar. 25, 1974.

SUMMARY OF THE INVENTION

According to the present invention, it has now been found that a congener of squalane, namely, 2,7,10,15,18,23-hexamethyltetracosane, has properties akin to those of squalane, is useful as a substitute for squalane, and is prepared unexpectedly more economically than is squalane.

This new compound according to the invention has the following structural formula, and physical and chemical characteristics:

Melting point: −91°−−93° C.
Boiling point: 227° C./1.0 mmHg∼233° C./1.7 mmHg
Index of refraction: $n_D^{25} = 1.4523$
Infrared spectrum, as shown in the figure of drawing.
Mass analysis reflected the $[M^+]$ to be 422; absorption peaks and the respective carbon atoms corresponding thereto, by means of NMR spectra utilizing $^{13}C$, were as follows:

TABLE I

| Absorption peak (ppm) | Corresponding carbon atom(s) |
|---|---|
| 19.41 | 9,13 |
| 22.36 | 1,3 |
| 23.95 | 5 |
| 27.01 | 6,15 |
| 27.45 | 2 |
| 32.58 | 8,12 |
| 33.89 | 10,11 |
| 36.61 | 7,14 |
| 38.07 | 4 |

In the above Table I, the numbering of the respective carbon atoms of the subject compound was as follows:

The conditions of measurement comprise:
SW (HZ) = 6000
AT (SEC) = 0.3
PD (SEC) = 1.0
PW (USEC) = 70
K-TRANS = 5
PTS = 3600

The object compound can be prepared as follows:

i. By the process for preparing said 2,7,10,15,18,23-hexamethyltetracosane which comprises hydrogenating either 2,7,10,15,18,23-hexamethyltetracosa-1,6,18,23-tetraene-11,13-diyne-10,15-diol (I) having the structural formula:

$$CH_2=C(CH_3)-(CH_2)_3-CH=CH-(CH_2)_2-CH(CH_3)-C\equiv C-C\equiv C-C(CH_3)(OH)-(CH_2)_2-C(CH_3)=CH-(CH_2)_3-C(CH_3)=CH_2 \quad (I)$$
(with OH on the C bearing the first CH_3 group after the diyne as shown)

cally than is squalane.

or 2,7,10,15,18,23-hexamethyltetracosa-11,13-diyne-10,15-diol (II) having the structural formula:

$$CH_3-C(CH_3)-(CH_2)_4-CH(CH_3)-(CH_2)_2-CH(CH_3)-C\equiv C-C\equiv C-C(CH_3)(OH)-(CH_2)_2-CH(CH_3)-(CH_2)_4-C(CH_3)-CH_3 \quad (II)$$

to the compound (III) having the structural formula:

$$CH_3-CH(CH_3)-(CH_2)_4-CH(CH_3)-(CH_2)_2-CH(CH_3)-(CH_2)_4-CH(CH_3)-(CH_2)_2-CH(CH_3)-(CH_2)_4-CH(CH_3)-CH_3;$$

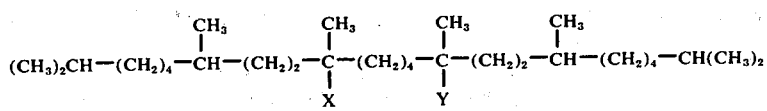

wherein X and Y represent hydrogen atoms or hydroxyl radicals, and wherein at least one of said X and Y necessarily is a hydroxyl radical, namely, the compounds (III) include the compounds, 2,7,10,15,18,23-hexamethyltetracosa-10,15-diol (IV) of 2,7,10,15,18,23-hexamethyltetracosa-10-ol (V), thence subjecting these latter compounds to dehydration and ultimately, subjecting the dehydrated precursors to hydrogenation.

In the case of preparation of the compounds (IV) or (V), the subject compound too may be obtained in a minor proportion, as by-product, but all such products can be utilized in the dehydration reaction which sequentially follows, without the need for any separation thereof.

ii. By the process for preparing 2,7,10,15,18,23-hexamethyltetracosane which comprises hydrogenolyzing the compounds (IV) or (V), or a mixture of the said compounds (IV) and (V), in the same manner as in [i].

iii. By the process for preparing 2,7,10,15,18,23-hexamethyltetracosane which comprises hydrogenating the compounds (I) or (II) to an unsaturated precursor which bears the hydroxyl radicals, but is devoid of acetylenic unsaturation, i.e., the triple bond is preferentially hydrogenated to provide the compound, 2,7,10,15,18,23-hexamethyltetracosa-1,6,11,13,18,23-hexaene-10,15-diol (VI) having the structural formula:

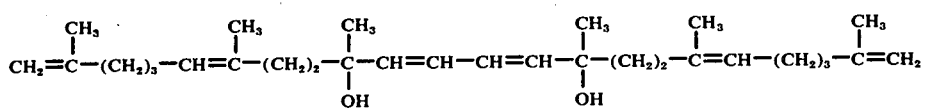

or 2,7,10,15,18,23-hexamethyltetracosa-11,13-diene-10,15-diol (VII) having the structural formula:

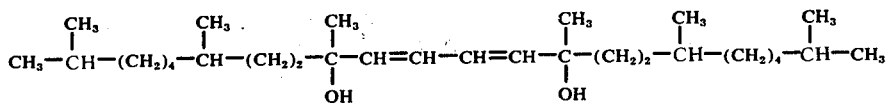

and thence subjecting these said compounds (VI) and/or (VII) to hydrogenolysis.

iv. By the process for preparing 2,7,10,15,18,23-hexamethyltetracosane which comprises subjecting the compound (I) or (II) to hydrogenolysis.

DETAILED DESCRIPTION OF THE INVENTION

Each of the aforesaid processes according to this invention will now be described in detail:

A. Synthesis of the Compounds (I) and (II)

The compound (I) according to the invention is a novel compound and can be prepared, for example, by reacting 5,10-dimethylundeca-5,10-dien-3-one with diacetylene, as follows:

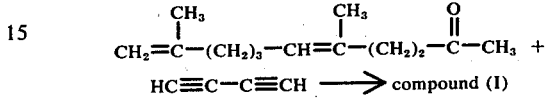

or, also, by reacting 5,10-dimethylundeca-5,10-dien-2-one with acetylene to obtain another novel compound, 3,6,11-trimethylundeca-6,11-dien-1-yn-3-ol, and thence subjecting this latter compound to oxidative coupling, as follows:

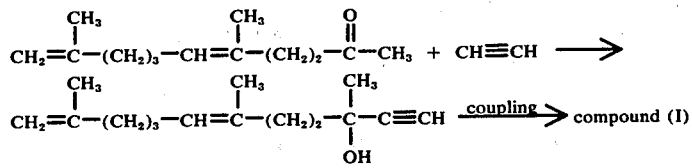

Among the starting materials which can be utilized in this invention, 5,10-dimethylundeca-5,10-dien-2-one is a known compound and can be prepared by reacting isoprene with acetoacetic ester in the presence of a catalytic palladium compound, followed by decarboxylation of the intermediate product [Japanese patent application No. Sho 47-25047/1972]. 5,10-dimethylundeca-2-one can also be prepared by hydrogenating the above 5,10-dimethylundeca-5,10-dien-2-one in the presence of a palladium catalyst supported on active carbon.

In the instances of reacting the 5,10-dimethylundeca-5,10-dien-2-one with either diacetylene or acetylene, and the 5,10-dimethylundeca-2-one with either diacetylene or acetylene, the usual synthetic methods comprising the known acetylenic alcohol technology can be broadly applied.

Preferred embodiments according to this invention are as follows:

1. 5,10-dimethylundeca-5,10-diene-2-one or 5,10-dimethylundeca-2-one is reacted with a Grignard reagent of either acetylene or diacetylene, in a solvent such as diethylether, typically used in the Grignard reaction.

2. An alkali metal or alkaline earth metal, such as lithium, sodium, potassium or calcium, is dissolved in liquid ammonia and acetylene or diacetylene gas is bubbled therein to form the corresponding acetylide, and 5,10-dimethylundeca-5,10-dien-2-one or 5,10-dimethylundeca-2-one is reacted with said acetylides.
3. Acetylene or diacetylene is reacted with 5,10-dimethylundeca-5,10-dien-2-one or 5,10-dimethylundeca-2-one in the presence of an alkali metal compound, such as potassium hydroxide, sodium hydroxide or sodium amide in liquid ammonia or in an organic solvent such as ether, dimethylformamide or tetrahydrofuran.

In the event of preparation of the compound (I) or (II) by means of molecular coupling of the 3,6,11-trimethyldodeca-6,11-diene-1-yn-3-ol or 3,6,11-trimethyldodeca-1-yn-3-ol, the usual oxidative coupling reaction can also be broadly applied. The preferred embodiments according to this invention, in this particular respect, are as follows:

1. A solution of 3,6,11-trimethyldodeca-6,11-diene-1-yn-3-ol or 3,6,11-trimethyldodeca-1-yn-3-ol in an organic solvent which is soluble in water, such as ethanol, acetone or tetrahydrofuran, is added to a solution of a cuprous salt such as cuprous chloride and ammonium chloride in water and the mixture is subjected to coupling in an atmosphere of oxygen. In this event, the reaction may be carried out in the presence of hydrochloric acid, ferric chloride or ammonia, as a reaction accelerator;
2. 3,6,11-trimethyldodeca-6,11-diene-1-yn-3-ol or 3,6,11-trimethyldodeca-1-yn-3-ol is added to a solution of a cuprous salt, such as cuprous chloride in an organic solvent such as pyridine or picoline, and is coupled in an atmosphere of oxygen;
3. 3,6,11-trimethyldodeca-6,11-diene-1-yn-3-ol or 3,6,11-trimethyldodeca-1-yn-3-ol is added to a solution of a cupric salt such as cupric acetate in an organic solvent such as pyridine or picoline.

B. Hydrogenation of the Compound (I) or (II)

The typical hydrogenation reactions can be utilized for the aforesaid hydrogenations characterized as [i] and [iii].

In the case of the said above method [i], for example, palladium or platinum metal supported on active carbon, Raney nickel or Raney cobalt, or palladium, platinum, rodium, ruthenium, indium, or osmium metal, or the corresponding metal oxides thereof, or such metals or metal oxides supported on a suitable carrier, can be used as the hydrogenation catalyst.

By hydrogenation of the compound (I) by means of the method [i], the compound (IV), 2,7,10,15,18,23-hexamethyltetracosa-10,15-diol, or the compound (V), 2,7,10,15,18,23-hexamethyltetracosa-10-ol, or a mixture of these compounds, or a mixture of these said compounds and the object compound according to the invention, are obtained, albeit the precise compositional profile of the reaction product depends on the type of catalyst utilized, the amount thereof, the solvent employed and the reaction temperature used for said hydrogenation reaction.

It is preferred to carry out the complete hydrogenation reaction at relatively elevated temperatures, namely, at or above 100° C., to significantly enhance the rate of reaction.

With respect to the phenomenon of either cleaving or retaining intact the said hydroxyl radicals during the course of the reaction, the following have been generally observed: When a catalyst such as Raney metal type catalyst, exhibiting such basicity as Raney nickel, is utilized, and, as to the reaction solvent, a low polarity solvent is used, and the reaction is carried out at lower temperatures, the hydroxyl radicals are very difficultly removed. In order to provide the subject diol, it is, therefore, preferred to carry out the hydrogenation using such a catalyst as Raney nickel, in a low polarity liquid saturated hydrocarbon, and under milder conditions of temperature. When utilizing conditions under which the hydroxyl radicals are much more readily cleaved or removed, such side-reactions as cyclization of the product occur and it is, consequently, much more difficult to obtain the object compound of the invention in a high degree of purity.

The method [iii], as aforesaid, relates to a process for preparing the object compound by hydrogenation of the compound (I) or (II) under milder conditions, by selectively hydrogenating only the sites of acetylenic unsaturation, thus rendering any remaining sites of ethylenic unsaturation less active, followed by hydrogenolysis of such intermediate product, whereby hydrogen atoms are substituted for hydroxyl radicals and, simultaneously, any remaining sites of ethylenic unsaturation are concomitantly hydrogenated. The products thus prepared contain almost no by-product, which by-product is difficult to separate by, e.g., distillation. Accordingly, the purity of the products produced by this method [iii] is, therefore, very high.

As catalysts used for the hydrogenation of this method, [iii], the catalysts employed for the method [i] can also be used, but, in view of the stronger hydrogenating activity under the milder temperature conditions, and from an economical point of view, Raney nickel, Raney cobalt or palladium supported on active carbon, barium sulfate or calcium carbonate, are particularly preferred.

The hydrogen pressure during the hydrogenation is sufficient if same is under a hydrogen pressure of below about 100 kg/cm$^2$; the reaction can even be conducted below the normal pressures.

It is preferred that the hydrogenation reaction be carried out in a suitable solvent, because of the high viscosity of the compounds (I) and (II). Any organic solvent can be used, so long as the solvent does not hinder or interfere with the hydrogenation reaction. For example, fatty hydrocarbons, aromatic hydrocarbons, ethers, esters, alcohols and organic acids can be employed, but the amines and the sulfur-containing compounds are not preferred. The amount of the solvent employed is sufficient if same is present in an amount at least as great as that of the respective intermediates, but same may be utilized in lesser amounts, if the dispersion of catalyst into the solvent is sufficiently high.

C. Dehydration and Hydrogenation of the Compounds (IV) and (V) or a Mixture of Same Respecting the dehydration reaction of the intermediates obtained by means of the above method [i], by removing the tertiary hydroxyl radicals borne by the reaction intermediates, the following catalysts are exemplary:
a. A br$\phi$nsted acid such as sulfuric acid, hydrochloric acid, phosphoric acid, perchloric acid or boric acid;
b. A Lewis acid, such as zinc chloride, aluminum chloride, boron trifluoride or stannic chloride;

c. A hydrogen salt of a strong acid and a strong base, such as sodium hydrogen sulfate, sodium hydrogen phosphate or potassium hydrogen sulfate;
d. A salt of a strong acid and a weak base, such as magnesium sulfate, zinc sulfate, potassium sulfate, copper sulfate or magnesium chloride;
e. A solid acid, such as silica-alumina, alumina, solid phosphoric acid or cationic ion-exchange resin.

The topic reaction can be carried out in the presence of a solvent as above described, in the absence of solvent, or in a solution of said dehydrated compounds in a suitable solvent. In the presence of such a mineral acid as sulfuric acid or phosphoric acid, of such a Lewis acid as zinc chloride or aluminum chloride, or of such a cationic ion-exchange resin, utilized as catalyst, the dehydration reaction can be conducted substantially quantitatively in the presence of a solvent such as an organic acid, a hydrocarbon, a primary alcohol, an ether or a ketone, or, under milder conditions of temperature, i.e., below 200° C., in the absence of such solvents. Contrariwise, in the presence of such a solid catalyst as alumina, silica-alumina, or active silica, the reaction is preferably conducted at a temperature in the range of about 150° to 300° C. in order to effect the dehydration in a shorter period of time. The thus obtained dehydration intermediate provides the object compound according to the invention by means of the same hydrogenation technique, under the same conditions as outlined concerning the above method (A).

D. Hydrogenolysis of the Compound (I) or (II) and the Partially Hydrogenated Compound (VI) or (VII)

The hydrogenolysis reaction in accordance with the foregoing methods [ii], [iii] and [iv] can be conducted at elevated temperatures by adding an acidic material such as typically employed for dehydration reactions, to the usual hydrogenation reaction system. The catalysts used for hydrogenolysis are the metal catalysts, such as nickel, palladium, platinum, rhodium and iridium, or the metal compounds thereof, e.g., their oxide forms, or these metals or compounds thereof can be utilized supported on a suitable carrier. The hydrogenolysis reaction employing such a catalyst can be carried out, for example, as follows:

1. The reaction can be carried out in an organic carboxylic acid.

Among said carboxylic acids, acetic acid, propionic acid, lactic acid and isolactic acid are the preferred. Other, more acidic acids, such as the α-halogenofatty acids and the α-hydroxyfatty acids may be used, in combination with the aforesaid organic carboxylic acids;

2. The method reaction can be carried out in the presence of certain acidic substances, in an inert organic solvent. Exemplary preferred organic solvents which may be used include hexane, heptane, cyclohexane, ethylcyclohexane, decaline, hexadecaline, squalane, or the object compound of the invention. The aromatic hydrocarbons, cyclic ethers, esters, ketones, and the alcohols, especially the tertiary alcohols, are subject to hydrogenation, cyclization, hydrolysis or dehydration under certain conditions and, thus, it is preferred that their use be avoided under such conditions.

Exemplary, effective "acidic substances" include:
a. A Brønsted acid, such as sulfuric acid, hydrochloric acid, phosphoric acid, perchloric acid or boric acid;
b. A Lewis acid, such as zinc chloride, aluminum chloride, boron trifluoride, or stannic chloride;
c. A hydrogen salt of a strong acid and a strong base, such as sodium hydrogen sulfate, sodium hydrogen phosphate, or potassium hydrogen sulfate;
d. A salt of a strong acid and a weak base, such as magnesium sulfate, zinc sulfate, calcium sulfate, copper sulfate or magnesium chloride;
e. A solid acid, such as silica-alumina, alumina or solid phosphoric acid;
f. An organic acid, such as acetic acid, oxalic acid, monochloroacetic acid or lactic acid.

Regarding the effect of the combination of the catalyst and the acidic substance, or the catalyst, acidic substance and solvent, upon the foregoing method of hydrogenolysis, it is preferred that a combination system be utilized in which the catalyst is not especially subject to poisoning or dissolution in the acidic substance and/or solvent.

For this reason, and in view of the desirability of utilizing industrially available and economical catalysts, the following hydrogenolysis techniques are recommended:

a. Hydrogenolysis conducted in the presence of a nickel or palladium catalyst, suitably supported on a typical carrier, for example, nickel catalyst supported on diatomaceous earth, or palladium on active carbon; also in the presence of a salt of a strong acid and a weak base, or in the presence of a solid acid in the absence of solvent, or in the presence of an inert organic solvent.

b. Hydrogenolysis conducted in the presence of a palladium catalyst supported on a carrier such as active carbon, in an organic carboxylic acid, or in a mixed solvent of an organic carboxylic acid and an inert organic solvent compatible therewith.

Upon hydrogenolysis according to the aforesaid methods, the reaction can be conducted in liquid phase, at elevated temperatures. It is preferred that the reaction temperature be above 100° C., especially in the range of about 150° to 300° C. in view of the favorable effect upon reaction rate which results.

Respecting the hydrogen pressure, the reaction can be carried out under atmospheric pressure, but it is preferred that same be carried out under elevated pressures, usually under a hydrogen pressure of about 10 to 100 kg/cm$^2$ (gauge pressure). The amount of catalyst used depends on the particular type of same, but typically is in the range of about 0.1 to 10 weight %, based upon the amount by weight of the intermediate compound being subjected to hydrogenolysis.

The object compound thus produced by any of the above methods is a useful additive, carrier or base material for the various cosmetics and also is a useful lubricant for precision machinery.

In order to further illustrate the present invention and the advantages thereof, the following specific examples are given, it being understood that same are presented merely as illustrative and in no wise limitative.

EXAMPLE 1

Into a 5 liter three-necked and round-bottomed flask, about 2 liters of liquid ammonia were placed and 46 g of sodium metal were dissolved therein under a reflux of liquid ammonia; then 50 g of diacetylene were added to the solution. Upon completion of this reaction of the sodium with the diacetylene, 77.7 g of 5,10-dimethylundeca-5,10-dien-2-one (V) were added to the reaction solution. Further, dry ether was next added thereto and the liquid ammonia was gradually replaced with the ether and, finally, an additional 3 liters of ether were added thereto and, after the temperature within the reaction system attained 20° C., the reaction was continued for 2 hours. Under cooling of the reaction mixture, 160 g of ammonium chloride were added gradually and, upon neutralizing the mixture, 500 ml of water were added, and the water layer decanted. The organic layer was washed with water and dried with anhydrous sodium sulfate; upon evaporation of the ether 894 g of reaction mixture were obtained. This reaction product was subjected to silica gel liquid chromatography and 4.51 g of the unreacted (V) and 4.82 g of the product (I-1) were obtained.

Elementary analysis of this product revealed:

|   | Found | Calculated |
|---|-------|------------|
| C | 81.91 | 82.14 |
| H | 10.55 | 10.57 |
| O | 7.37  | 7.29  |

Mass analysis indicated that $[m]^+$ to be 438 and this value is consistent with that of 2,7,10,15,18,23-hexamethyltetracosa-1,6,18,23-tetraene-11,13-diyne-10,15-diol.

Into a 5 liter round-bottomed flask, 884 g of the ethynylation product and 1700 ml of n-heptane were placed, and 88 g of 3% Pd/C were added thereto. The mixture was hydrogenated at 60° C. for 5 hours under an atmosphere of hydrogen. The catalyst was filtered off from the reaction mixture and after distillation of the n-heptane, 931 g of reaction mixture were obtained. This product was subjected to reduced distillation to afford (A) 263 g boiling in the range 79°–81° C./0.8 mmHg; (B) 290 g boiling in the range 215°–217° C./0.16 mmHg, as the main distillate, besides forerun, middle distillate and distillation residue. The distillate (A) was shown to be a saturated ketone by infrared spectra and was considered to be 5,10-dimethylundeca-2-one, by the results of elementary analysis.

Elementary analysis of the distillate (A):

|   | Found | Calculated |
|---|-------|------------|
| C | 78.55 | 78.72 |
| H | 13.34 | 13.21 |
| O | 8.15  | 8.07  |

According to the results of gas chromatography, the distillate (B) was almost a unitary distillate and contained a few impurities in the lower boiling point range. Mass analysis and NMR spectra revealed that this product was almost entirely 2,7,10,15,18,23-hexamethyltetracosa-10,15-diol (IX) and same was then subjected to dehydration.

Into a 2 liter round-bottomed flask were placed 100 g of the distillate (B), 5 g of zinc chloride and 500 ml of n-heptane, the mixture was heated under reflux, and the water produced in the reaction as an azeotropic mixture with n-heptane was removed. The reaction mixture was washed with water and dried with anhydrous sodium sulfate and filtered. To the filtrate were added 10 g of 3% Pd/C and the mixture was stirred overnight at 200° C. under a hydrogen pressure of 100 kg/cm², in an autoclave. The catalyst was filtered off from the reaction mixture and the n-heptane was distilled off to obtain 54.6 g of product having a boiling point in the range 197°–202° C./1.1 mmHg. NMR spectra and infrared spectra of this product showed same to be a saturated hydrocarbon and this was confirmed to be 2,7,10,15,18,23-hexamethyltetracosane (IV) by the results of elementary analysis.

Elementary analysis:

|   | Found | Calculated |
|---|-------|------------|
| C | 85.14 | 85.22 |
| H | 14.80 | 14.78 |

EXAMPLE 2

Into a 3 liter round-bottomed flask was placed about 1 liter of liquid ammonia and 23 g of sodium metal were added thereto and dissolved therein. At temperatures ranging from −70° to −50° C., acetylene gas was bubbled therethrough and, upon completion of the reaction of the sodium metal with the acetylene, 194 g of 5,10-dimethylundeca-5,10-dien-2-one (V) were added to the reaction solution and the mixture was subjected to reaction for 8 hours under a reflux of liquid ammonia. 80 g of ammonium chloride were added to the reaction mixture and the ammmonia was distilled off; to the residue were added 500 ml of water and 500 ml of n-hexane. The organic layer was next decanted and washed with water; the n-hexane was distilled off from the organic layer to thus provide 240 g of crude 3,6,11-trimethyldodeca-6,11-diene-1-yn-3-ol.

To a 1 liter round-bottomed flask were added 48 g of the aforesaid crude product, and 500 ml of pyridine and 20 g of cuprous chloride were added thereto and the mixture was subjected to reaction at 60° C. for 3 hours under an atmosphere of oxygen. The pyridine was distilled off and to the residue 500 ml of benzene were added, and the solution was washed with an aqueous 3N—H₂SO₄ solution, repeatedly, and the benzene was then distilled off to afford 36.8 g of a very viscous liquid. The NMR spectra of this liquid are consistent with those of 2,7,10,15,18-23-hexamethyltetracosa-1,6,18,23-tetraene-11,13-diyne-10,15-diol (II) obtained in Example 4.

In a 1 liter autoclave, a mixture of 35 g of the thus obtained product, 350 ml of ethyl alcohol and 1.75 g of 3% Pd/C was hydrogenated overnight, at 100° C. under a hydrogen pressure of 5 kg/cm². The reaction mixture was treated in the same manner as in Example 1 and 26.2 g of viscous product were obtained. According to gas chromatography, this product consisted essentially of three portions and the portion (C), which had the shortest holding time in the gas chromatography technique, was consistent with the structure of 2,7,10,15,18,23-hexamethyltetracosane (IV) prepared in Example 1.

The portion (D) which had the longest holding time by gas chromatography, reflected the structure 2,7,10,15,18,23-hexamethyltetracosa-10,15-diol (IX).

Therefore, the middle portion (E), between (C) and (D), was reasoned to reflect the structure 2,7,10,15,18,23-hexamethyltetracosa-10-ol (X).

The ratios among the areas (C), (E) and (D) determined by gas chromatography were 12.4, 30.8 and 56.8%, respectively.

In a 200 ml round-bottomed flask, a mixture of 20 g of this hydrogenated product, 10 ml of Amberlyst-15 and 50 ml of toluol was subjected to dehydration for 3 hours, under a toluol reflux, and the water thus produced was removed as an azeotropic mixture with said toluol. The Amberlyst-15 was next removed from the reaction mixture and the toluol solution was then washed with water, repeatedly.

Further, to this reaction solution 150 ml of toluol and 2 g of 3% Pd/C were added and the mixture was thence hydrogenated at 200° C., under a hydrogen pressure of 100 kg/cm$^2$ in a 300 ml autoclave. The reaction mixture was treated in the same manner as in Example 1 and after evaporation of the toluol, 13.2 g of viscous product were obtained. This product was confirmed to be 2,7,10,15,18,23-hexamethyltetracosane (IV), obtained as in Example 1, by means of gas chromatography and NMR spectra.

EXAMPLE 3

In a 1 liter round-bottomed flask, about 250 ml of liquid ammonia, 5.8 g of sodium metal and 6.3 g of diacetylene were reacted, and, upon completion of the reaction of the sodium with the diacetylene, 99.2 g of 5,10-dimethylundeca-2-one (VII), prepared as in Example 1, were added to the mixture and the liquid ammonia was replaced with 250 ml of dry ether; the mixture was next treated in the same manner as in Example 1 and 112 g of crude product were obtained. 10 g of this crude product were subjected to liquid chromatography and 4.0 g of unreacted product (VII) and 3.9 g of reaction product were obtained.

Elementary analysis of this product:

|   | Found | Calculated |
|---|-------|------------|
| C | 80.46 | 80.65 |
| H | 12.20 | 12.18 |
| O | 7.20  | 7.16 |

Mass analysis indicated [M]$^+$ to be 446 and this value was consistent with that of 2,7,10,15,18,23-hexamethyltetracosa-11,13-diyne-10,15-diol (II).

Then, there were placed in a 2 liter round-bottomed flask, 102 g of ethynylation product, 1000 ml of n-heptane and 5 g of 3% Pd/C and the mixture was subjected to hydrogenation and treated thereafter in the same manner as in Example 1; the thus obtained product was identified with the product obtained in Example 1 and was confirmed to be the same product.

EXAMPLE 4

About 500 ml of liquid ammonia was placed in a 2 liter round-bottomed flask and 11.5 g of sodium metal were dissolved therein, and acetylene gas was bubbled therethrough at temperatures from $-70°$ to $-50°$ C. After completion of the reaction of the sodium metal with the acetylene, 99.2 g of 5,10-dimethylundeca-2-one (VII), prepared as in Example 1, were added to the reaction mixture. 500 ml of dry ether were also added thereto and the liquid ammonia was gradually distilled off. After the temperature of the reaction system reached 20° C., the reaction was continued for 30 minutes and, ultimately completed by adding thereto 40 g of ammonium chloride. 250 ml of water were next added to the reaction system, the water layer was decanted, and the organic layer was repeatedly washed with water and lastly dried. The ether was distilled off to provide 123 g of crude reaction product. This was purified by means of silica gel liquid chromatography and 7.8 g of crude product were obtained.

Elementary analysis of this product was as follows:

|   | Found | Calculated |
|---|-------|------------|
| C | 80.16 | 80.29 |
| H | 12.60 | 12.58 |
| O | 7.09  | 7.13 |

This product was confirmed to be 6,11-trimethyldodeca-1-yn-3-ol (VIII) by infrared spectra and mass analysis.

Into a 1 liter round-bottomed flask, there were placed 50 g of the crude product obtained via ethynylation, and same was subjected to oxidative coupling and thereafter treated in the same manner as in Example 2. 35.4 g of viscous liquid were thus obtained. The NMR spectra of this product was consistent with those of 2,7,10,15,18,23-hexamethyltetracosa-11,13-diyne-10,15-diol (II) obtained as in Example 3.

EXAMPLE 5

About 3 liters of liquid ammonia were placed into a 5 liter round-bottomed flask and 69.0 g of sodium metal were added thereto and dissolved therein. The solution was cooled to $-70°$ C. and acetylene was bubbled therethrough; upon complete formation of the sodium acetylide, 583 g of 5,10-dimethylundeca-5,10-dien-2-one were added thereto. The mixture was reacted under a reflux of liquid ammonia for 8 hours in the presence of a minor flow of acetylene. Crude 3,6,11-trimethyldodeca-6,11-diene-1-yn-3-ol was next prepared in the same manner as in Example 2.

This crude product, 2 liters of n-heptane, 60 ml of pyridine and 27.2 g of anhydrous copper acetate were placed in a 5 liter round-bottomed flask and the mixture was reacted at 70°–80° C. for 8 hours under an oxygen blanket. The reaction mixture was then washed with an aqueous 3N—H$_2$SO$_4$ solution and thence repeatedly with water. After distilling off almost all of the n-heptane, 1216 g of crude product were obtained.

100 g of this crude product were placed in a 500 ml autoclave; 100 ml of n-heptane and 5 g of 5% Pd/C were added to the autoclave and the mixture was reacted overnight at 100° C. under a hydrogen pressure of 50 to 100 kg/cm$^2$. Upon removing the Pd/C catalyst from the reaction mixture, the filtrate was placed in an autoclave and 5 g of 50% nickel on diatomaceous earth and 5 g of silica-alumina catalyst, consisting of about 30% alumina, were added thereto. The mixture was subjected to hydrogenolysis at 230° C., under a hydrogen pressure of 80 to 100 kg/cm$^2$, overnight, and 2,7,10,15,18,23-hexamethyltetracosane was thus obtained. The yield was confirmed to be 39.5 g by means of quantitative measurement with gas chromatography.

EXAMPLE 6

Into a 500 ml autoclave there were placed 100 g of the crude 1216 g of oxidative coupling product obtained in Example 5, and 7 ml of Raney nickel and 100 ml of n-heptane were added thereto and the mixture was hydrogenated overnight at temperature of from room temperature to 50° C. under a hydrogen pressure of 50 to 100 kg/cm$^2$. After completion of the reaction, the Raney nickel was filtered off and the filtrate was repeatedly washed with water. NMR analysis of this solution using $^{13}C$ revealed that the compound contained in the solution was devoid of acetylenic, but not ethylenic, unsaturation. This solution was then placed in an autoclave and 5 g of 50% nickel diatomaceous earth and 5 g of silica-alumina, containing 30% alumina, were added thereto. The mixture was subjected to hydrogenolysis in the same manner as in Example 6, and 37.7 g of 2,7,10,15,18,23-hexamethyltetracosane were thus obtained.

EXAMPLE 7

Into a 500 ml autoclave there were placed 100 g of the crude 1216 g of oxidative coupling product obtained in Example 5. 5 g of the 50% nickel diatomaceous earth and 0.5 g of the silica-alumina utilized in Example 5 were next added thereto. The mixture was subjected to hydrogenolysis under the same conditions as in the Examples 5 and 6, and 37.3 g of 2,7,10,15,18,23-hexamethyltetracosane were thus obtained.

While the invention has been described and illustrated with reference to certain preferred embodiments thereof, those skilled in the art will appreciate that various changes, modifications and substitutions therein can be made without departing from the spirit of the invention. It is intended, therefore, that the invention be limited only by the scope of the claims which follow.

What is claimed is:

1. A compound 2,7,10,15,18,23-hexamethyltetracosane.

* * * * *